(12) United States Patent
Johnson et al.

(10) Patent No.: US 10,562,022 B2
(45) Date of Patent: Feb. 18, 2020

(54) MECHANICALLY ACTUATED VACUUM CONTROLLED FLUID COLLECTION

(71) Applicant: Boston Microfluidics, Inc., Boston, MA (US)

(72) Inventors: Brandon T. Johnson, Somerville, MA (US); Kate E. Christian, Cambridge, MA (US); Glenn H. Verner, Powell, OH (US)

(73) Assignee: Boston Microfluidics, Inc.

( * ) Notice: Subject to any disclaimer, the term of this patent is extended or adjusted under 35 U.S.C. 154(b) by 0 days.

(21) Appl. No.: 15/864,051

(22) Filed: Jan. 8, 2018

(65) Prior Publication Data

US 2018/0154351 A1    Jun. 7, 2018

Related U.S. Application Data

(63) Continuation of application No. 14/098,280, filed on Dec. 5, 2013, now Pat. No. 9,861,978.

(60) Provisional application No. 61/733,516, filed on Dec. 5, 2012.

(51) Int. Cl.
*B01L 3/00* (2006.01)
*A61B 10/00* (2006.01)

(52) U.S. Cl.
CPC ............ *B01L 3/502* (2013.01); *A61B 10/007* (2013.01); *B01L 2200/16* (2013.01); *B01L 2300/0832* (2013.01); *B01L 2300/0864* (2013.01); *B01L 2400/0478* (2013.01)

(58) Field of Classification Search
CPC ............... B01L 3/502; B01L 2200/16; B01L 2300/0832; B01L 2300/0864; B01L 2400/0478; A61B 10/007
See application file for complete search history.

(56) References Cited

U.S. PATENT DOCUMENTS

| | | | | |
|---|---|---|---|---|
| 3,430,813 A | * | 3/1969 | Gilmont | B01L 3/0282 222/309 |
| 3,767,085 A | | 10/1973 | Cannon et al. | |
| 4,257,267 A | * | 3/1981 | Parsons | B01L 3/0234 222/309 |
| 4,386,606 A | | 6/1983 | Tretinyak et al. | |
| 4,690,005 A | * | 9/1987 | Tervamaki | B01L 3/0224 422/925 |

(Continued)

*Primary Examiner* — Robert J Eom
(74) *Attorney, Agent, or Firm* — David J. Thibodeau, Jr.; VLP Law Group LLP

(57) ABSTRACT

A mechanically-actuated vacuum-controlled fluid collection system includes a mechanically-actuated vacuum controller (MAVC) to draw fluid into a chamber through the opening to the chamber. The system may include a releasable seal to seal the opening, and the MAVC may include a spring-loaded plunger to create a vacuum within the chamber when sealed. The system includes multiple fluid chambers, and may further include a single actuator or multiple corresponding actuators. The system may be configured to add a pre-loadable reagent to fluid drawn into the one or more chambers, and may be configured to add the reagent in proportion to a volume of the fluid. The system may be controllable to release collected fluid to another device, such as for assay and/or transport. The system may be configured to draw a liquid biological sample such as urine, and may include a fluid interface to draw fluid from a biological sample container.

20 Claims, 10 Drawing Sheets

(56) References Cited

U.S. PATENT DOCUMENTS

| | | |
|---|---|---|
| 4,915,695 A | 4/1990 | Koobs |
| 5,013,667 A | 5/1991 | Lynn et al. |
| 6,106,779 A | 8/2000 | Buechler et al. |
| 6,120,733 A | 9/2000 | Goodman et al. |
| 6,524,864 B2 | 2/2003 | Decastro |
| 7,803,319 B2 | 9/2010 | Yang et al. |
| 7,838,258 B2 | 11/2010 | Yang et al. |
| 8,105,554 B2 | 1/2012 | Kanigan et al. |
| 8,173,380 B2 | 5/2012 | Yang et al. |
| 8,206,650 B2 | 6/2012 | Samsoondar |
| 8,329,119 B2 | 12/2012 | Pearcy et al. |
| 8,561,795 B2 | 10/2013 | Schott |
| 8,741,230 B2 | 6/2014 | Holmes et al. |
| 8,808,202 B2 | 8/2014 | Brancazio |
| 8,821,412 B2 | 9/2014 | Gonzalez-Zugasti |
| 8,827,971 B2 | 9/2014 | Gonzalez-Zugasti |
| 8,940,539 B2 | 1/2015 | Pearcy et al. |
| 8,986,983 B2 | 3/2015 | Monatgu et al. |
| 9,023,292 B2 | 5/2015 | Rostaing et al. |
| 9,033,898 B2 | 5/2015 | Chickering et al. |
| 9,040,236 B2 | 5/2015 | Hill et al. |
| 9,041,541 B2 | 5/2015 | Levinson et al. |
| 9,113,836 B2 | 8/2015 | Bernstein et al. |
| 9,119,578 B2 | 9/2015 | Haghgooie et al. |
| 9,176,126 B2 | 11/2015 | Holmes et al. |
| 9,289,763 B2 | 3/2016 | Berthier et al. |
| 9,295,417 B2 | 3/2016 | Haghgooie et al. |
| 9,386,948 B2 | 7/2016 | Holmes et al. |
| 9,427,184 B2 | 8/2016 | Holmes et al. |
| 9,636,062 B2 | 5/2017 | Holmes et al. |
| 9,987,629 B2 | 6/2018 | Berthier et al. |
| 2011/0127294 A1* | 6/2011 | Pearcy ............... A61J 1/2089 422/501 |
| 2013/0211289 A1 | 8/2013 | Moga et al. |

\* cited by examiner

1000

MECHANICALLY ACTUATED VACUUM CONTROLLED FLUID COLLECTION

CROSS REFERENCE TO RELATED APPLICATIONS

This application is a continuation of co-pending U.S. patent application Ser. No. 14/098,280 filed Dec. 5, 2013 which claims the benefit of U.S. Provisional Patent Application No. 61/733,516, filed Dec. 5, 2012, each of which are incorporated herein by reference in their entirety.

BACKGROUND

Conventional fluid collection devices are not portable, mechanically actuated, and/or designed to collect a measured amount of liquid, interface with a liquid biological sample container, a transport device, and/or an assay device, and/or to add a pre-loaded reagent to collected fluid.

Figure 1A:
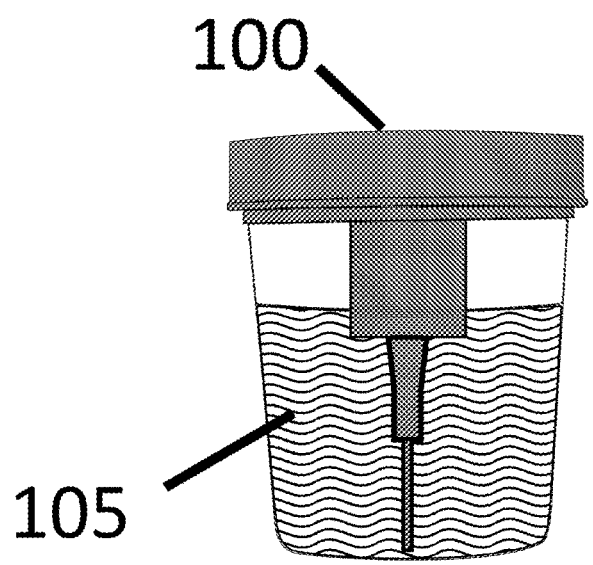
FIG. 1A illustrates a fluid collection device having a built-in sample collection interface to collect liquid or fluid.

In the drawings, the leftmost digit(s) of a reference number identifies the drawing in which the reference number first appears.

DETAILED DESCRIPTION

Disclosed herein are mechanically actuated vacuum fluid collection systems and methods.

FIG. 1A illustrates a fluid collection device 1000 having a built-in sample collection interface 100, to collect liquid or fluid 105. Fluid collection device 1000 may be configured and/or serve as a fluid collection device, such as to collect a biological fluid, such as urine, from a container or cup.

Figure 1B:
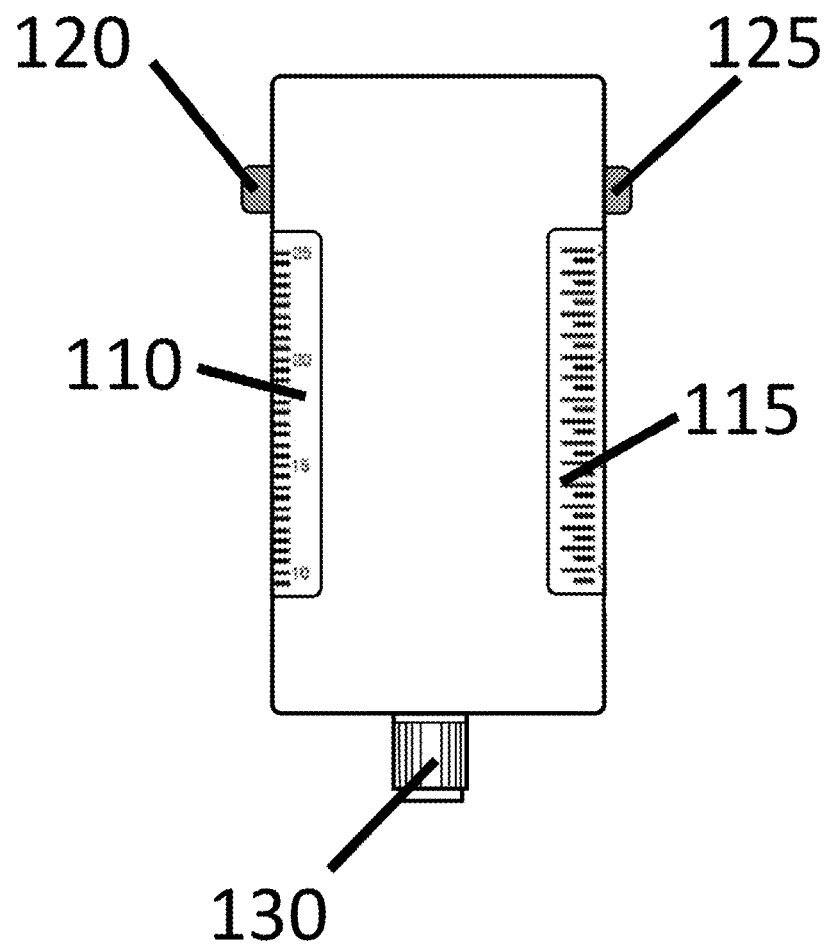
FIG. 1B is a front view of the fluid collection device of FIG. 1A.

FIG. 1B is a front view of fluid collection device 1000, including syringe units 110 and 115 and triggers 120 and 125 that are mechanically activated to initiate fluid collection by syringe units 110 and 115, respectively. A sample port 130 connects to sample collection interface 100 (FIG. 1A), to permit fluid communication between fluid sample 105 (FIG. 1A) and syringe units 120 and 125 when activated. Sample port 130 may include, without limitation, a straw, a pierceable membrane, a Luer lock, and/or or a one-way valve.

Figure 1C:
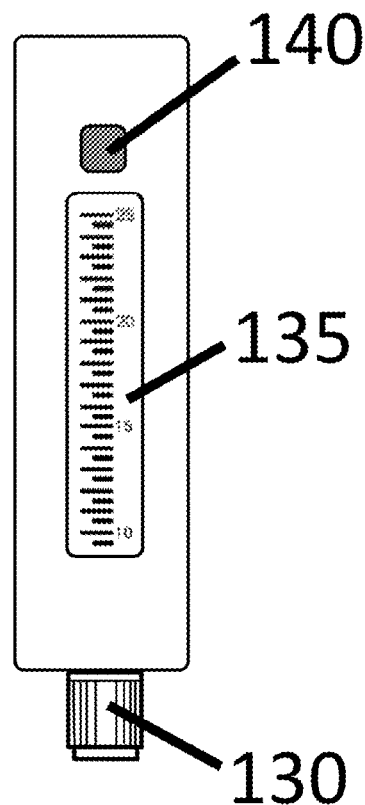
FIG. 1C is a side profile of the fluid collection device of FIG. 1A.

FIG. 1C is a side profile of fluid collection device 1000, including sample port 130, syringe unit 110, and corresponding trigger 120.

Fluid collection device 1000 may be configured as described with respect to one or more examples described below. Fluid collection device 1000 is not, however, limited to any of the examples below.

Figure 2:
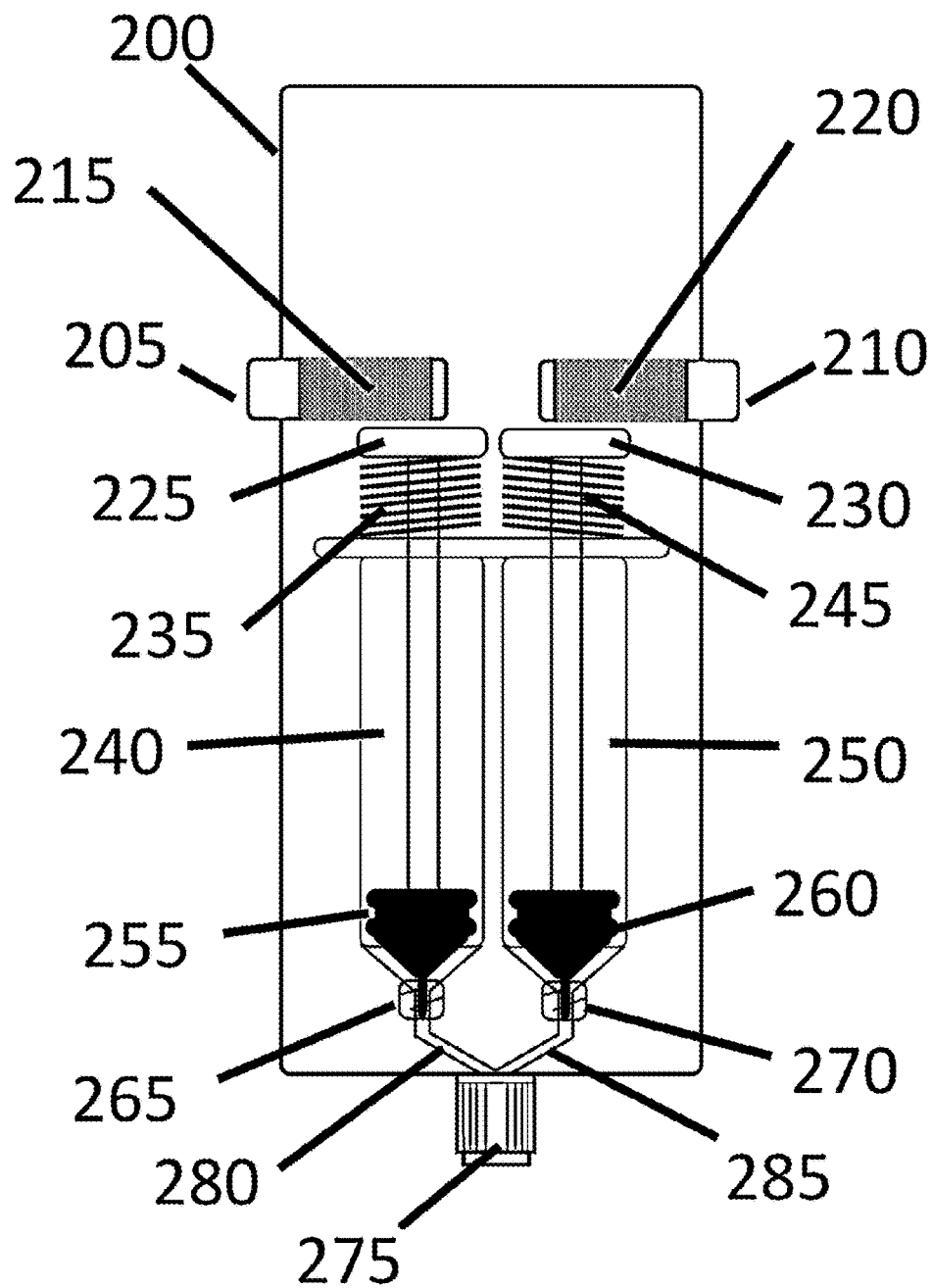
FIG. 2 is a cut-away front view of another fluid collection device.

FIG. 2 is a cut-away front view of a fluid collection device 2000, including an outer case 200, which may be removable. Outer case 200 may be shorter, relative to device 1000, than illustrated in FIG. 2.

Triggers 205 and 210 have openings 215 and 220 at their centers that, when corresponding triggers 205 and 210 are mechanically actuated, allow plungers 225 and 230 to rise, respectively.

Device 2000 may include springs spring 235 and 245 to provide a force for fluid collection. When trigger 205 is activated, spring 235 extends and pushes plunger 225 up through an opening 215 to create a vacuum to draw a fluid sample into a chamber, illustrated here as a syringe unit 240. When trigger 210 is activated, spring 245 extends and pushes plunger 230 up through opening 220 to create a vacuum to draw fluid into syringe unit 250. Triggers 205 and 210 may be actuated in tandem or in series.

Device 2000 may be configured to interface with a fluid collection container such as, for example, a urine collection container. Device 2000 may include stoppers 255 and 260 to form seals around inlets of syringe units 240 and 250, respectively.

Device 2000 may include adaptors 265 and 270 to connect syringe units 240 and 250 to sample port 275 via fluid channels 280 and 285, respectively. Adaptors 265 and 270 may include a Luer interface with fluid channels 280 and 285, respectively. Sample port 275 may include a rubber septum.

Fluid collection device 2000 may be configured as described with respect to one or more other examples described herein. Fluid collection device 2000 is not, however, limited to other examples herein.

Figure 3:
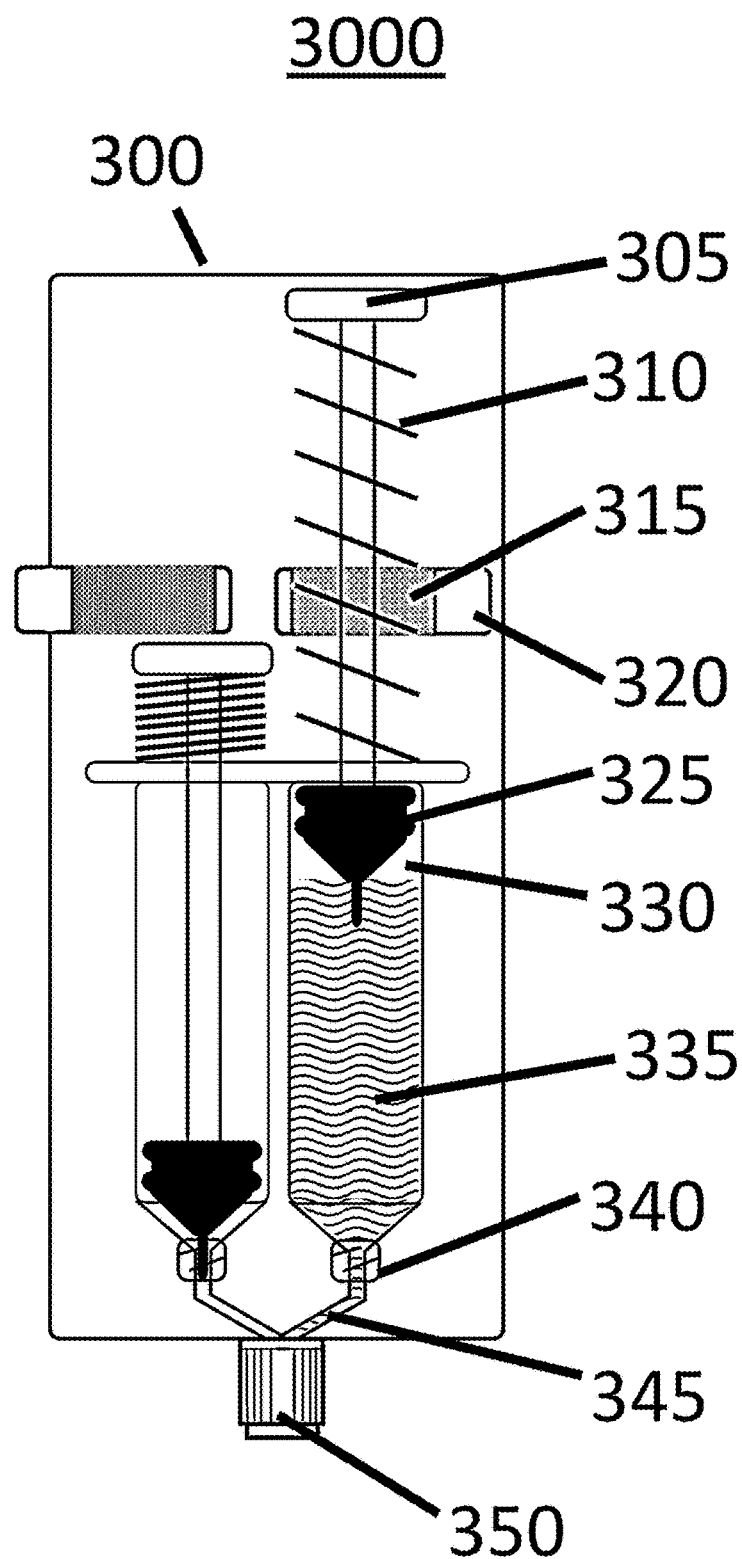
FIG. 3 is a cut-away front view of another fluid collection device after one of two syringe units has been activated.

FIG. 3 is a cut-away front view of a fluid collection device 3000 after one of two syringe units has been activated.

A plunger 305 has been extended by expansion of a spring 310 through an opening 315 following activation of a trigger 320. A stopper 325 has been drawn through syringe unit 330 and fluid sample 335 has been collected by suction.

An adaptor 340 connects a body of a syringe unit to a channel 345 that interfaces with a sample port 350, which is in fluid communication with a fluid sample.

Components of device 3000 may be contained within outer case 300.

Fluid collection device 3000 may be configured as described with respect to one or more other examples described herein. Fluid collection device 3000 is not, however, limited to other examples herein.

Figure 4:
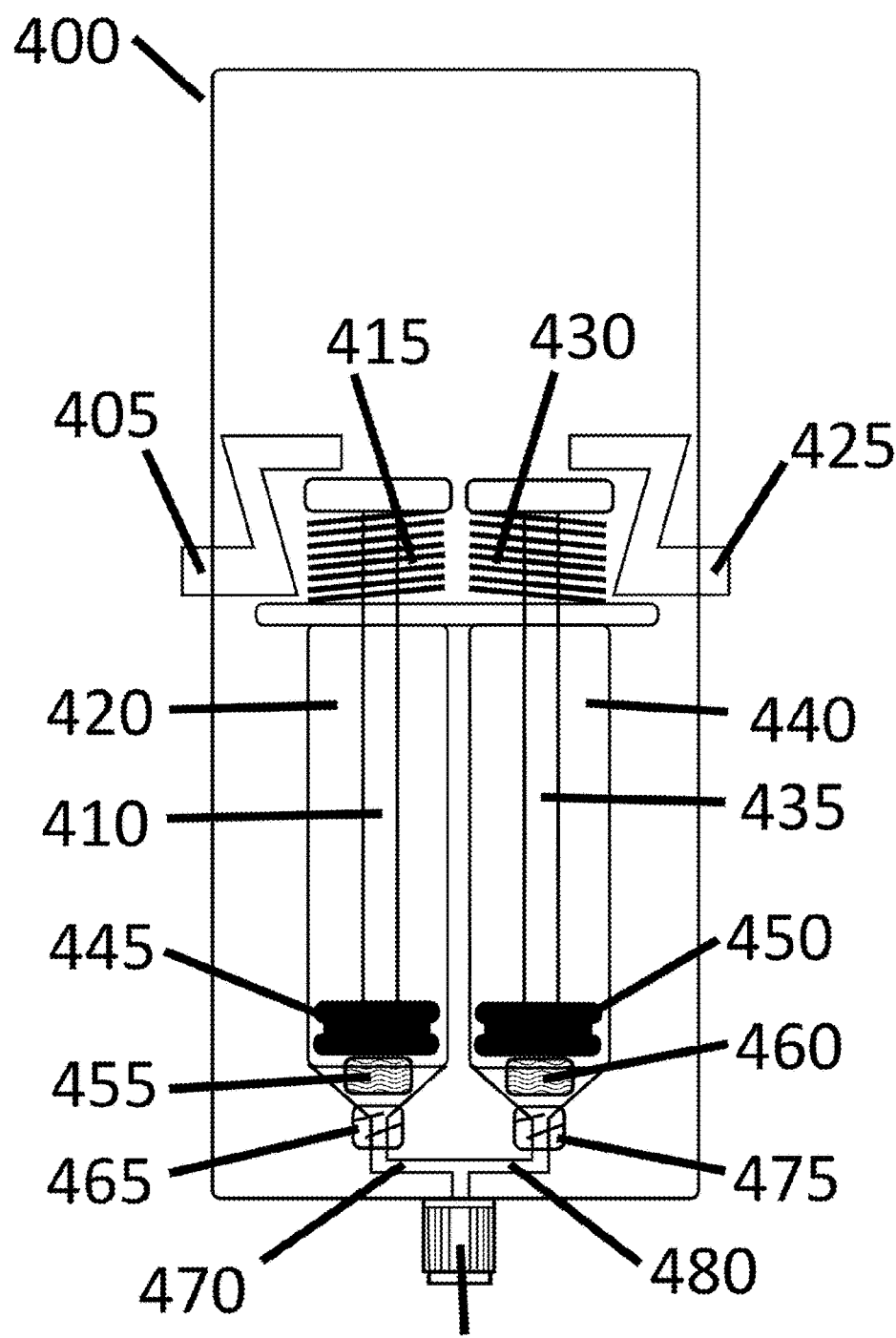
FIG. 4 is a cut-away front view of another fluid collection device that is preloaded with a reagent.

FIG. 4 is a cut-away front view of a fluid collection device 4000 that is preloaded with a reagent and includes a variation of an activation trigger. When activated, a trigger 405 releases a plunger 410 and a force from spring 415 causes it to extend and create a vacuum in a syringe unit 420. When a trigger 425 is activated, it allows a spring 430 to push up on a plunger 435, extending it and creating a vacuum in a syringe unit 440.

Syringe units 420 and 440 may be sealed with stoppers 445 and 450, respectively. In FIG. 4, syringe unit 420 contains a reagent 455, and syringe unit 440 contains reagent 460. As fluid is drawn into the syringe units, the fluid combines with reagents 455 and 460 to create a homogenous mixture. Syringe units 420 and 440 may be actuated in tandem or in series.

In an embodiment a volume of the fluid collected may be predetermined and/or measured.

In an embodiment a volume of the reagent may be predetermined and/or measured.

In FIG. 4, an adaptor 465 connects fluid channel 470 to syringe unit 420, and an adaptor 475 connects fluid channel 480 to syringe unit 440. Fluid channels 470 and 480 interface with sample port 485, which is in fluid communication with the fluid sample.

Components of device 4000 may be contained within outer case 400.

Fluid collection device 4000 may be configured as described with respect to one or more other examples described herein. Fluid collection device 4000 is not, however, limited to other examples herein.

Figure 5:
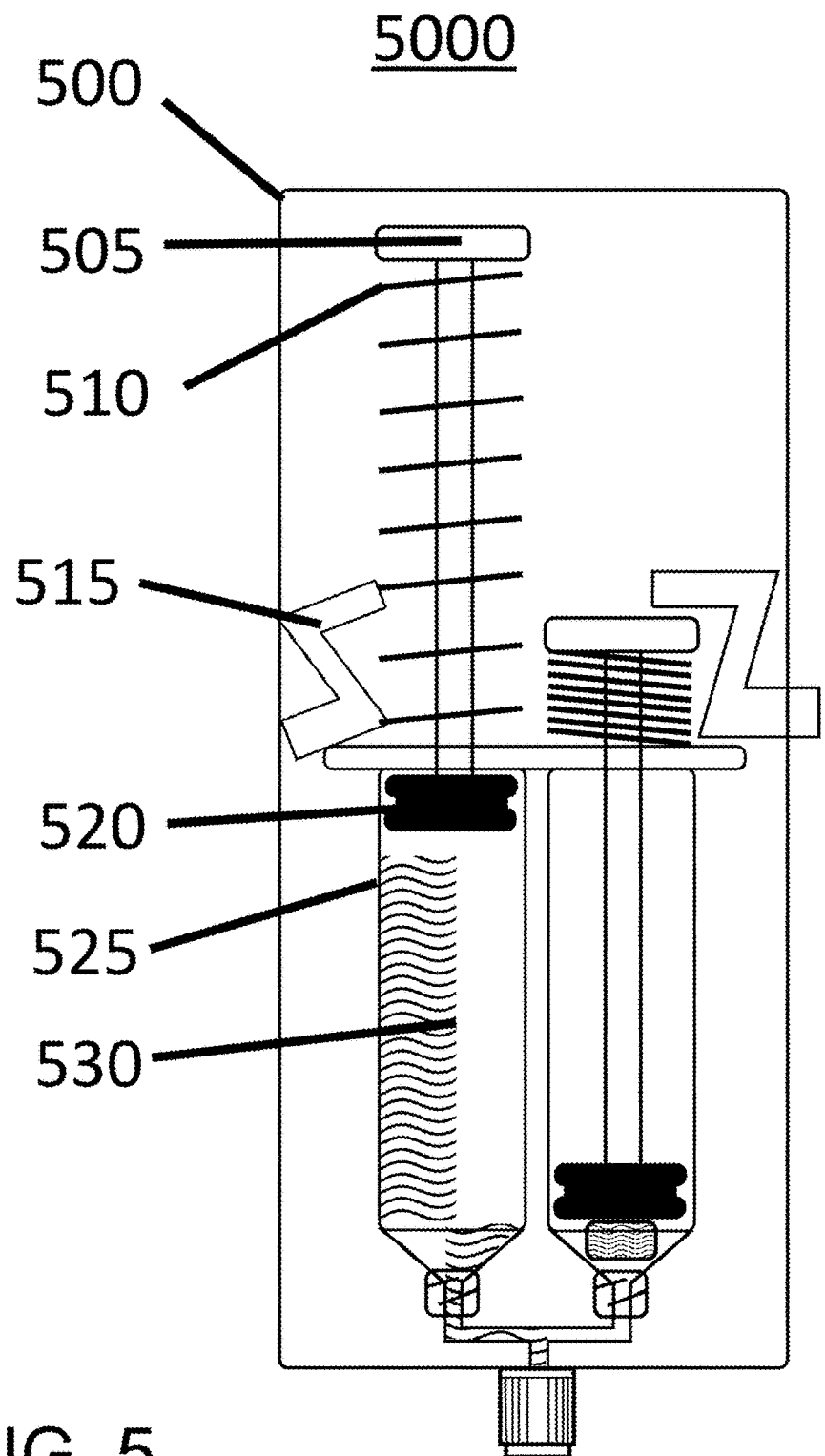
FIG. 5 is a cut-away front view of another fluid collection device that is preloaded with a reagent.

FIG. 5 is a cut-away front view of a fluid collection device 5000 that is preloaded with a reagent and includes a variation of a trigger after one syringe unit has been activated. A plunger 505 has been extended by a spring 510 following mechanical activation of a trigger 515. A stopper 520 has been drawn up through syringe unit 525, filling it with fluid sample 530. A preloaded reagent mixes with a fluid 530 as it is drawn into syringe unit 525, to provide a homogenous solution of sample and reagent.

Components of device 5000 may be contained within outer case 500.

Fluid collection device 5000 may be configured as described with respect to one or more other examples described herein. Fluid collection device 5000 is not, however, limited to other examples herein.

Figure 6A:
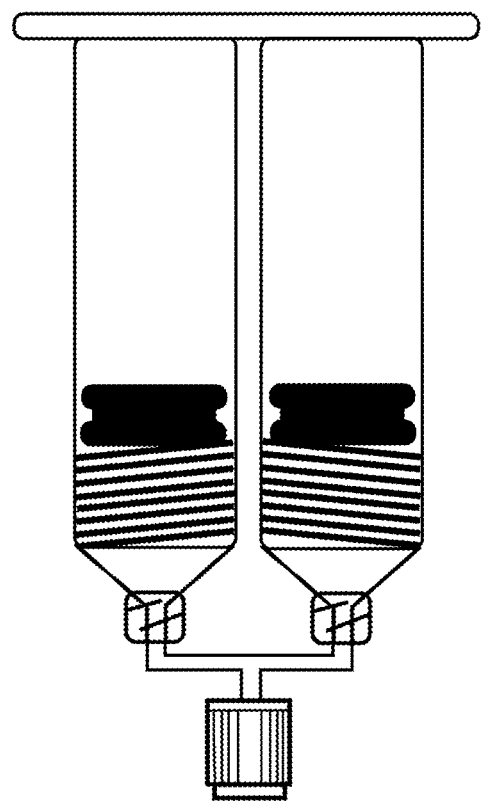
FIG. 6A is a cut-away front-view view of another fluid collection device having a two-stage plunger system and a preloaded reagent which may be added to a collected fluid in multiple installments.

FIG. 6A is a cut-away front-view view of a fluid collection device 6000, having a two-stage plunger system and a preloaded reagent which may be added in multiple installments. Fluid collection device 6000 may be configured as described below with reference to FIG. 6B and/or FIG. 6C.

Figure 6B:
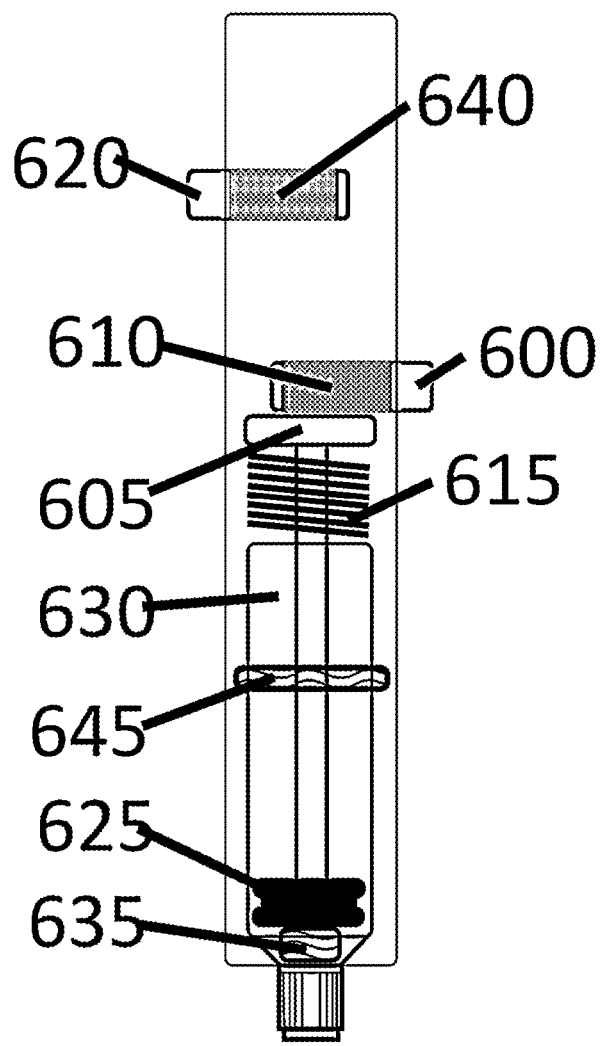
FIG. 6B is a cut-away side-view of an embodiment of the fluid collection device of FIG. 6A.

FIG. 6B is a cut-away side-view of an embodiment of fluid collection device 6000. When a trigger 600 is mechanically activated, it moves to allow a plunger 605 to pass through an opening 610 in trigger 600. A spring 615 extends plunger 605 until it comes into contact with a trigger 620, which has not yet been activated. A stopper 625 is drawn back by this action and a syringe unit 630 fills with a first portion of fluid sample. A reagent 635 mixes with the sample as is enters syringe unit 630. The amount of sample and/or reagent may be measured and/or predetermined.

Trigger 620, when pushed, activates a second stage of the plunge. It allows plunger 605 to pass through an opening 640 and further extend using force from a spring 615. As stopper 625 moves past a reagent deposit 645, an additional portion of fluid is drawn up and added to the previously-collected portion of sample.

Triggers 600 and 620 may be actuated sequentially, in that order, or trigger 600 only may be actuated.

Figure 6C:
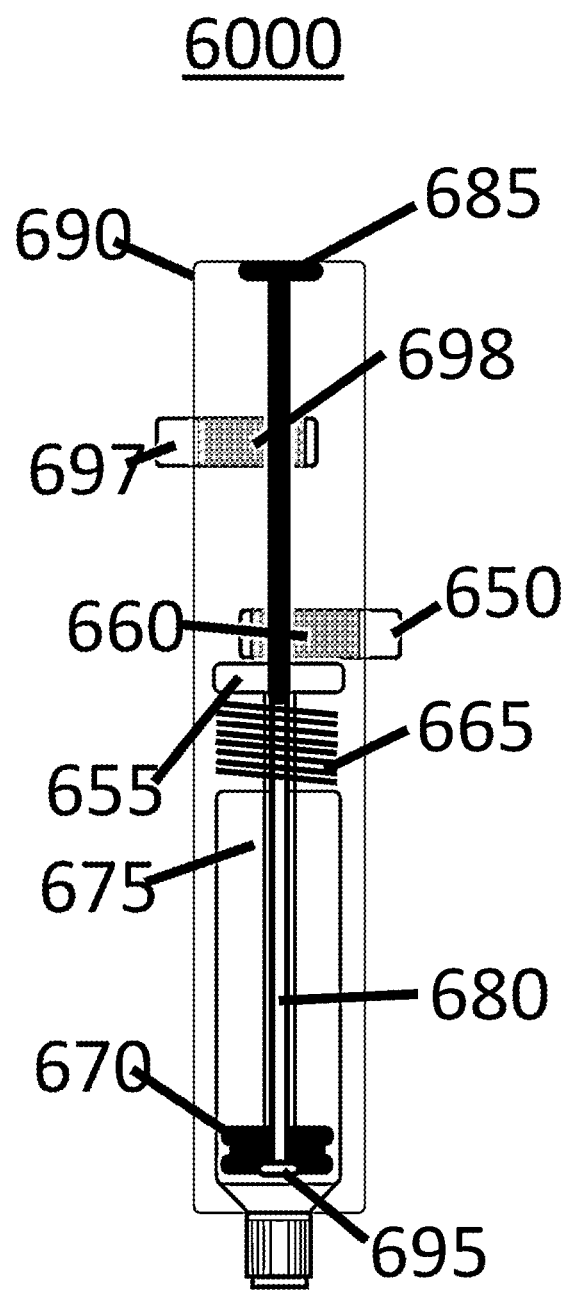
FIG. 6C is a cut-away side-view of another embodiment of the fluid collection device of FIG. 6A.

FIG. 6C a cut-away side-view of another embodiment of fluid collection device 6000, having a preloaded reagent that is added proportionally to the fluid sample being collected.

When a trigger 650 is actuated, a plunger 655 extends through an opening 660 by force of a spring 665. This draws back a stopper 670 and fills a syringe unit 675 with fluid sample. A reagent 680 is forced out of a hollowed plunger 655 as it moves upward into a solid plunger 685, which is fixed to an outer device case 690. As this happens, a one-way valve 695 adds reagent 680 proportionally to the fluid sample to provide a mixed solution. Valve 695 may include a stopper.

A trigger 697 activates a second stage of the plunge and collection of an additional portion of fluid sample by allowing plunger 655 to pass through an opening 698 by the force of spring 665. Upward movement of hollowed plunger 655 moves it upward onto solid plunger 685, which pushes reagent 680 out of one-way valve 695. Reagent 680 is forcibly mixed with the fluid sample to provide a homogenous mixture.

Triggers 650 and 697 may be activated sequentially, in that order, or trigger 650 alone may be activated.

A device as disclosed herein may be configured to collect a liquid or fluid that includes a biological sample such as, without limitation, a urine sample.

A device as disclosed herein may include a push-button to actuate a trigger.

A device as disclosed herein may include retractable plunger to create a vacuum in the device in order to collect a fluid.

A device as disclosed herein may include a spring configured to provide sufficient for to fill the device.

A device as disclosed herein may be configured to draw up portions of fluid in sequence and/or in parallel, and may be configured to accommodate one or more of a variety of volumes, which may include a measured volume and/or a predetermined volume.

A device as disclosed herein may include one or more sealable chambers for collection of fluid samples. The device may be configured, for example, to seal the samples for transport. A sealable chamber(s) may have more than one stop, with each stop collecting a portion of fluid. A sealable chamber may include a syringe.

In some embodiments, reagent may be added to these portions. The sample and reagent may be forcibly mixed in the sample collection chamber. In some embodiments the addition of reagent may be proportional to the amount of fluid collected.

A device as disclosed herein may be preloaded with a liquid reagent.

A device as disclosed herein may be preloaded with a dry reagent.

A device as disclosed herein may be configured to release and/or expel collected fluid, such as for assay and/or transport.

A device as disclosed herein may be configured to release and/or expel a portion of collected fluid.

A device as disclosed herein may be configured to release and/or expel a measured and/or adjustable amount of collected fluid.

A device as disclosed herein may include an openable external case to provide access to collected fluid.

A device as disclosed herein may be configured to release collected fluid by pushing a plunger.

A device as disclosed herein may include membrane or rubber septum, which may be punctured to release or expel collected fluid.

A device as disclosed herein may include a fluid interface to transfer collected fluid to a diagnostic or transport system.

A device as disclosed herein may include a fluid interface to draw fluid from a urine collection cup.

Methods and systems are disclosed herein with the aid of functional building blocks illustrating functions, features, and relationships thereof. At least some of the boundaries of these functional building blocks have been arbitrarily defined herein for the convenience of the description. Alternate boundaries may be defined so long as the specified functions and relationships thereof are appropriately performed. While various embodiments are disclosed herein, it should be understood that they are presented as examples. The scope of the claims should not be limited by any of the example embodiments disclosed herein.

The invention claimed is:

1. A fluid collection device, comprising:
a housing having a fluid chamber configured to receive, measure and retain a fluid and an opening to the fluid chamber;
a mechanically-actuated, non-adjustable vacuum controller to draw in a fixed, predetermined amount of the fluid into the fluid chamber through the opening, the predetermined amount of fluid being fixed by either a part of the housing, or a part disposed within the housing, the part thereby limiting an extent to which the vacuum controller draws in fluid;
the mechanically-activated vacuum controller being further configured to thereby store the fixed, predetermined volume of fluid in the fluid chamber, as the fixed, predetermined volume of fluid is drawn sequentially through the opening and then into the fluid chamber by the mechanically-actuated vacuum controller; and
the fluid chamber further configured to hold the fixed, predetermined amount of fluid for transport within the device.

2. The device of claim 1 additionally comprising:
a reagent chamber, the reagent chamber disposed within the housing, and preloaded with a fixed, predetermined amount of a reagent prior to activation of the mechanically-actuated, non-adjustable vacuum controller.

3. The device of claim 2 wherein the reagent chamber is configured to hold a fixed, predetermined amount of a liquid reagent.

4. The device of claim 2, wherein the fluid chamber has multiple sealable fluid chambers to receive a collection of mixed fluid and reagent samples.

5. The device of claim 2, wherein the mechanically-actuated, non-adjustable vacuum controller is configured to add reagent in proportion to volumes of multiple portions of measured fluid.

6. The device of claim 2, wherein the reagent chamber is preloaded with a liquid reagent.

7. The device of claim 2, wherein the reagent chamber is preloaded with a dry reagent.

8. The device of claim 2, wherein mixed fixed, predetermined amounts of fluid and reagent stored within the fluid chamber are only accessible by opening the housing.

9. The device of claim 2, further including:
a mechanical actuator to actuate the mechanically-actuated vacuum controller, wherein a portion of the mechanical actuator extends through a surface of the housing to permit a user to actuate the mechanically-actuated vacuum controller; and
wherein the reagent and the mechanically-actuated vacuum controller are pre-disposed within the housing, inaccessible to the user.

10. The device of claim 1, wherein the mechanically-actuated, non-adjustable vacuum controller is configured to draw a biological sample fluid into the fluid chamber through the opening.

11. The device of claim 1, wherein the mechanically-actuated, non-adjustable vacuum controller further includes a push-button based actuator to actuate the mechanically-actuated, non-adjustable vacuum controller.

12. The device of claim 1, further including a fluid stopper, disposed within or on the housing, to releasably seal the opening to the fluid chamber for transport of the fixed, predetermined amount of fluid.

13. The device of claim 12, wherein the mechanically-actuated, non-adjustable vacuum controller includes a plunger to create a vacuum within the fluid chamber when the fluid stopper is engaged to seal the opening.

14. The device of claim 13, wherein the mechanically-actuated, non-adjustable vacuum controller includes a spring to apply a mechanical force to the plunger.

15. The device of claim 14, wherein the mechanically-actuated, non-adjustable vacuum controller further comprises a push button to trigger the mechanically-actuated, non-adjustable vacuum controller to draw fluid into the fluid chamber through the opening, the push button having an opening through which the plunger passes when the push button is triggered.

16. The device of claim 1, wherein the mechanically-actuated, non-adjustable vacuum controller is configured to draw in and retain multiple fixed, predetermined volumes of fluid into the fluid chamber sequentially or in parallel.

17. The device of claim 1, wherein the fixed, predetermined amount of fluid is only accessible by opening the housing.

18. The device of claim 1, further including one or more of a pierce-able membrane and rubber septum disposed over the opening.

19. The device of claim 1, configured to interface with a diagnostic or transport system.

20. The device of claim 1 wherein the mechanically-actuated vacuum controller further comprises:
a plunger to create a vacuum within the fluid chamber; and
a mechanical actuator to actuate the plunger, wherein the mechanical actuator is connected to the plunger to control a position of the plunger,
wherein the part of the housing, or the part disposed within the housing, thereby controls movement of the plunger to only move by a fixed, non-adjustable, predetermined distance within the fluid chamber, and
wherein the mechanical actuator is predisposed within the housing, inaccessible to a user of the device.

* * * * *